United States Patent
Mocaer

(10) Patent No.: US 7,622,505 B2
(45) Date of Patent: Nov. 24, 2009

(54) ASSOCIATION BETWEEN AGOMELATINE AND A NORADRENALINE REUPTAKE INHIBITOR, AND PHARMACEUTICAL COMPOSITIONS CONTAINING IT

(75) Inventor: Elisabeth Mocaer, Neuilly-sur-Seine (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 11/516,877

(22) Filed: Sep. 7, 2006

(65) Prior Publication Data

US 2007/0060654 A1 Mar. 15, 2007

(30) Foreign Application Priority Data

Sep. 9, 2005 (FR) .................. 05 09206

(51) Int. Cl.
*A61K 31/16* (2006.01)
(52) U.S. Cl. .................. 514/630
(58) Field of Classification Search ........ 514/288, 514/630
See application file for complete search history.

(56) References Cited

U.S. PATENT DOCUMENTS 6,096,742 A * 8/2000 Crocker et al. .............. 514/241

2006/0205754 A1 * 9/2006 Willigers .............. 514/288

FOREIGN PATENT DOCUMENTS

WO 2005/002562 1/2005

OTHER PUBLICATIONS

Ban et al. Clinical efficacy of reboxetine: a comparative study with desipramine, with methodological considerations. Human Psychopharmacology, vol. 13, pp. S29-S39, 1998.*
Chilman-Blair, et al., "Agomelatine. Antidepressant treatment of bipolar disorder melatonin agonist/5-HT20 antagonist", Drugs of the Future, vol. 28, No. 1, p. 7-13, Jan. 2003.
Versiani, M., "The selective noraderenaline re-uptake inhibitor reboxetine has an early onset of antidepressant action", International Journal of Psychiatry in Clinical Practice, vol. 4, No. 4, p. 293-297, 2000.
Fleishaker, J.K., "Clinical pharmacokinetics of reboxetine, a selective norepinephrine reuptake inhibitor for the treatment of patients with depression", Clinical Pharmacokinetics, vol. 39, No. 6, p. 413-427, 2000.
French Preliminary Search Report for 05.09206 of Apr. 28, 2006.
Sussman, N., "SNRIs Versus SSRIs: Mechanisms of Action in Treating Depression and Painful Physical Symptoms", *Primary Care Companion, J. Clin. Psychiatry*, 2003, 5 (Suppl 7), 19-26.

* cited by examiner

*Primary Examiner*—Jennifer Myong M Kim
(74) *Attorney, Agent, or Firm*—Hueschen and Sage

(57) ABSTRACT

Association comprising agomelatine, or N-[2-(7-methoxy-1-naphthyl)ethyl]acetamide, in association with a noradrenaline reuptake inhibitor agent.

Medicinal products containing the same which are useful in treating conditions associated with mood disorders.

3 Claims, No Drawings

ASSOCIATION BETWEEN AGOMELATINE AND A NORADRENALINE REUPTAKE INHIBITOR, AND PHARMACEUTICAL COMPOSITIONS CONTAINING IT

The present invention relates to a new association between agomelatine, or N-[2-(7-methoxy-1-naphthyl)ethyl]acetamide of formula (I):

or its hydrates, crystalline forms and addition salts with a pharmaceutically acceptable acid or base, and a noradrenaline reuptake inhibitor agent or any agent capable of increasing the concentration of noradrenaline at the extracellular level, for obtaining pharmaceutical compositions useful in the treatment of depression and, more especially, in the treatment of resistant depressions.

Agomelatine, or N-[2-(7-methoxy-1-naphthyl)ethyl]acetamide, has the double characteristic of being, on the one hand, an agonist of receptors of the melatoninergic system and, on the other hand, an antagonist of the 5-HT$_{2c}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, and appetite disorders and obesity.

Agomelatine, its preparation and its use in therapeutics have been described in European Patent Specification EP 0 447 285.

The Applicant has now found that agomelatine, or N-[2-(7-methoxy-1-naphthyl)ethyl]-acetamide or its hydrates, crystalline forms and addition salts with a pharmaceutically acceptable acid or base, used in association with a noradrenaline reuptake inhibitor agent, has valuable properties allowing its use in the treatment of major depressive disorder, seasonal affective disorder and, more especially, in the treatment of resistant depressions, and also in the treatment of psychiatric co-morbidity associated with mood disorder anxiety, panic, stress, sleep disorders . . .

Disorders of the central nervous system, such as depression and anxiety, affect a large number of people of all ages. Although many effective molecules exist in that field, none of them allows those various pathological states to be fully cured and some of them have significant side effects. Accordingly, the development of new alternative treatments is ongoing and continues to be a necessity. This is especially true in the case of patients who are totally resistant to all treatments. A conventional so-called "strategy of association" consists of combining a plurality of treatments having different mechanisms of action in order to obtain a positive effect. As a general rule, the beneficial effect observed is patient-dependent and arises from the response to one or another of the compounds of the association.

The most conventional associations described in the literature are concerned with associations with mood stabilisers, such as lithium, with other antidepressants either of different clinical profile or of different neurochemical profile.

The Applicant has now discovered, surprisingly, that the effects of agomelatine are potentiated by noradrenaline reuptake inhibitor agents, or by agents capable of increasing the concentrations of noradrenaline at the extracellular level. Those agents have the characteristic of potentiating the effects of agomelatine.

That unpredictable effect allows the use of the association to be considered in the treatment of major depressive disorder, seasonal affective disorders and, more especially, in the treatment of resistant depressions, as well as of psychiatric co-morbidity associated with mood disorder: anxiety, panic, stress, and sleep disorders. Even more especially, that potentiation of the effects will allow the use of the association according to the invention in the treatment of patients resistant to all treatments.

Among the noradrenaline reuptake inhibitor agents according to the invention there may be mentioned, more especially and without implying any limitation, reboxetine and desipramine.

The noradrenaline reuptake inhibitor agent preferred according to the invention is reboxetine.

The invention accordingly relates to the use of the association between agomelatine or its hydrates, crystalline forms and addition salts with a pharmaceutically acceptable acid or base, and a noradrenaline reuptake inhibitor compound or a compound capable of increasing the concentration of noradrenaline at the extracellular level in obtaining pharmaceutical compositions intended for the treatment of major depressive disorder, seasonal affective disorder and, more especially, resistant depressions, as well as in the treatment of psychiatric co-morbidity associated with mood disorder: anxiety, panic, stress, and sleep disorders.

The invention relates also to pharmaceutical compositions comprising the association between agomelatine or its hydrates, crystalline forms and addition salts with a pharmaceutically acceptable acid or base, and a noradrenaline reuptake inhibitor compound or a compound capable of increasing the concentration of noradrenaline at the extracellular level in combination with one or more pharmaceutically acceptable excipients.

Among the pharmaceutical compositions according to the invention there may be mentioned, more especially, those which are suitable for oral, parenteral or nasal administration, tablets or dragées, sublingual tablets, gelatin capsules, lozenges, suppositories, creams, ointments, dermal gels etc.

Besides agomelatine and the noradrenaline reuptake inhibitor compound, the pharmaceutical compositions according to the invention comprise one or more excipients or carriers selected from diluents, lubricants, binders, disintegration agents, absorbents, colourants, sweeteners etc.

By way of example, and without implying any limitation, there may be mentioned:
as diluents: lactose, dextrose, sucrose, mannitol, sorbitol, cellulose, glycerol,
as lubricants silica, talc, stearic acid and its magnesium and calcium salts, polyethylene glycol,
as binders: aluminium and magnesium silicate, starch, gelatin, tragacanth, methyl-cellulose, sodium carboxymethylcellulose and polyvinylpyrrolidone,
as disintegrants: agar, alginic acid and its sodium salt, effervescent mixtures.

The useful dosage varies according to the sex, age and weight of the patient, the administration route, the nature of the disorder and any associated treatments and ranges from 1 mg to 50 mg of agomelatine per 24 hours and is more preferably 25 mg per day. The dose of the noradrenaline reuptake inhibitor agent will be less than that used when it is administered on its own.

Pharmaceutical Composition:

Formula for the preparation of 1000 tablets each containing 25 mg of active ingredient:

| | |
|---|---|
| N-[2-(7-methoxy-1-naphthyl)ethyl]acetamide | 25 g |
| Lactose monohydrate | 62 g |
| Magnesium stearate | 1.3 g |
| Povidone | 9 g |
| Anhydrous colloidal silica | 0.3 g |
| Cellulose sodium glycolate | 30 g |
| Stearic acid | 2.6 g |

Clinical Study:

The clinical study is carried out in patients having major depressive disorder treated either with agomelatine and placebo or with agomelatine and reboxetine for a duration of 6 weeks. The diagnostic system used is that of DSM-IV; the principal criterion of efficacy is the total score of the Hamilton Rating Scale for Depression. A compilation of undesirable events is carried out. The study demonstrates a superior activity of the agomelatine-reboxetine association compared with agomelatine alone.

The invention claimed is:

1. A composition comprising a combination of agomelatine, or N-[2-(7-methoxy-1-naphthyl)ethyl]acetamide or crystalline forms and addition salts thereof with a pharmaceutically acceptable acid or base, and reboxetine, wherein the combination results in a potentiating effect.

2. A pharmaceutical composition comprising as active ingredient a composition of claim 1 alone or in combination with one or more pharmaceutically acceptable excipients.

3. A method for treating a living animal body, including a human afflicted with a condition selected from the group consisting of major depressive disorder, seasonal affective disorder, resistant depressions, and psychiatric co-morbidity associated with mood disorder: anxiety, panic, stress, sleep disorders comprising the step of administering to the living animal body, including a human, an amount of the composition of claim 1 which potentiates alleviation of the condition.

* * * * *